United States Patent [19]

Harada et al.

[11] Patent Number: 4,543,176

[45] Date of Patent: Sep. 24, 1985

[54] OXYGEN CONCENTRATION DETECTOR UNDER TEMPERATURE CONTROL

[75] Inventors: Takashi Harada, Hekinan; Akio Kobayashi, Kariya; Masakazu Honda, Anjo; Susumu Harada, Okazaki; Masaya Fujimoto, Oobu; Masatoshi Suzuki, Anjo, all of Japan

[73] Assignee: Nippondenxo Co., Ltd., Kariya, Japan

[21] Appl. No.: 585,861

[22] Filed: Mar. 2, 1984

[30] Foreign Application Priority Data

Mar. 8, 1983 [JP] Japan .................................. 58-37788

[51] Int. Cl.[4] ............................................. G01N 27/58
[52] U.S. Cl. .................................... 204/406; 123/489; 204/408; 204/425
[58] Field of Search ............... 204/406, 408, 425, 427, 204/428, 429, 15; 60/276; 123/489

[56] References Cited

U.S. PATENT DOCUMENTS

| | | | |
|---|---|---|---|
| 4,155,827 | 5/1979 | Maurer et al. ...................... | 204/428 |
| 4,332,225 | 6/1982 | Cox et al. ............................ | 123/440 |
| 4,359,030 | 11/1982 | Sone et al. .......................... | 123/440 |
| 4,376,026 | 3/1983 | Hoffman et al. .................... | 204/406 |
| 4,419,190 | 12/1983 | Dietz et al. ......................... | 204/1 T |
| 4,472,262 | 9/1984 | Kondo et al. ....................... | 204/408 |

FOREIGN PATENT DOCUMENTS 53-116896 10/1978 Japan .
57-48648 3/1982 Japan .
57-192852 11/1982 Japan .

OTHER PUBLICATIONS

Fracis Weston Sears et al., "College Physics", pp. 475-476, (1948).

Primary Examiner—G. L. Kaplan
Attorney, Agent, or Firm—Cushman, Darby & Cushman

[57] ABSTRACT

An oxygen concentration detector under a temperature control for an internal combustion engine. An oxygen sensor of a critical current type is held between a gas under test and a reference gas, in the vicinity of which a heater is located for heating up the oxygen sensor in a sensor activating temperature range. A first voltage is applied for a positive bias control to the oxygen sensor during a first period, and a second voltage is applied for a negative bias control thereto during a second period. Electric current flowing through the oxygen sensor is detected during the first period in order to detect the oxygen concentration in the gas under test. The current value is also detected during the second period in order to detect and maintain constant the internal electric resistance of the oxygen sensor by controlling the heater heating output.

10 Claims, 21 Drawing Figures

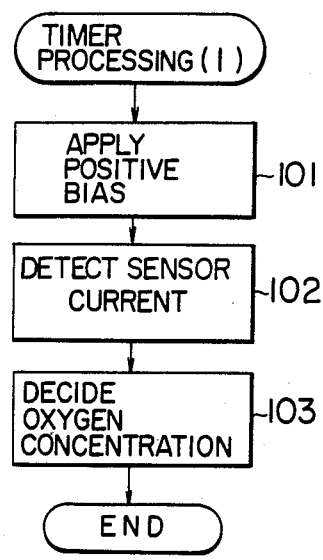
FIG. 5 a
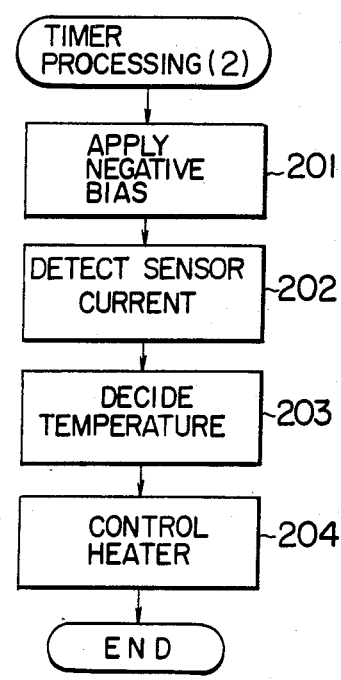
FIG. 5 b
FIG. 6
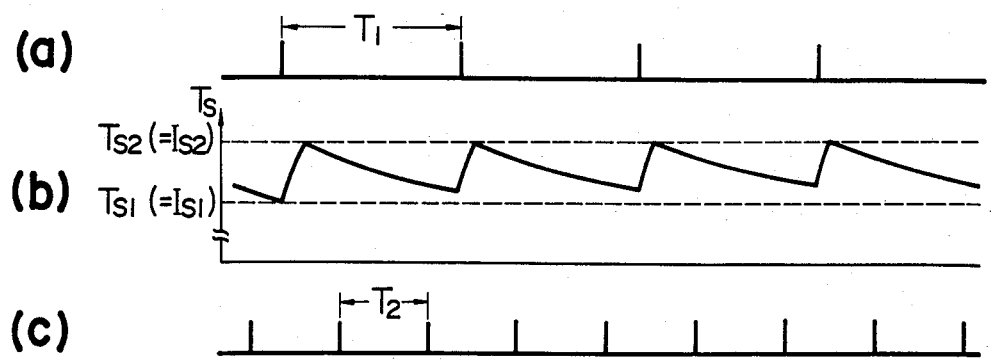

OXYGEN CONCENTRATION DETECTOR UNDER TEMPERATURE CONTROL

RELATED APPLICATION

The subject matter of this application is generally related to the subject matter of U.S. application Ser. No. 662,631, filed Oct. 19, 1984 and commonly assigned. These two applications claim different inventions.

BACKGROUND OF THE INVENTION

The present invention relates to an oxygen concentration detector for detecting the oxygen concentration in a medium such as the oxygen concentration (air-fuel ratio) in an exhaust gas of an internal combustion engine, or more in particular to a temperature control apparatus for the detector which is capable of satisfactorily detecting any air-fuel ratio more than a stoichiometric air-fuel ratio by use of an oxygen sensor of a critical current type current-limiting type.

A conventional apparatus of this type is disclosed in Japanese Patent Laid-Open specification No. 192852/82. Since the critical current characteristic of an oxygen concentration sensor of a critical current type changes with the temperature thereof, the sensor is required to be controlled within a predetermined activating range of temperature. In the sensor disclosed in the above Japanese Laid-Open specification, the sensor temperature is detected and controlled to a constant level by taking advantage of the fact that the internal electric resistance of the sensor changes with temperature. An AC voltage is used for measuring the internal resistance, while a DC voltage is used for measuring the critical current (that is, the oxygen concentration). Specifically, according to the embodiment shown in FIG. 14 of the Laid-Open specification, the critical current and the internal resistance are measured alternately in time division. In the case where the AC voltage is used for measuring the internal resistance, however, the calculation of the sensor temperature requires the processing of a complicated formula, and because of dependence on the frequency and duty factor of the AC voltage, an expensive peripheral device is required for high-precision detection, thereby leading to the disadvantage of high cost.

SUMMARY OF THE INVENTION

In view of the above-mentioned disadvantage, the object of the present invention is to provide an oxygen concentration detector under a temperature control for measuring the critical current and temperature alternately in time division by use of an oxygen concentration sensor of a critical current type current-limiting type, wherein a DC voltage is applied for negative bias instead of positive bias to the sensor for the measurement of the sensor temperature, thereby making possible a high-precision temperature control as well as a stable detection of oxygen concentration by a very simple construction.

According to the present invention, there is provided an oxygen concentration detector under a temperature control comprising an oxygen sensor made of a cup-shaped solid-electrolyte material, in which the interior of the cup is exposed to a standard (reference) gas of a predetermined oxygen concentration through a first electrode, while the exterior of the cup is exposed to a gas under test through a second electrode and a layer with a predetermined resistance against oxygen diffusion therethrough, whereby oxygen ions flowing from the interior toward the exterior of the cup can freely behave without undergoing restriction on account of absence of diffusion-resistant layer inside of the cup, and a linear resistance characteristic of the sensor is obtained with the negative bias, which resistance characteristic is associated with the sensor temperature.

BRIEF DESCRIPTION OF THE DRAWINGS

FIGS. 5 to 10 show flowcharts and signal waveforms for explaining the present invention.

DESCRIPTION OF THE PREFERRED EMBODIMENTS

Figure 1:
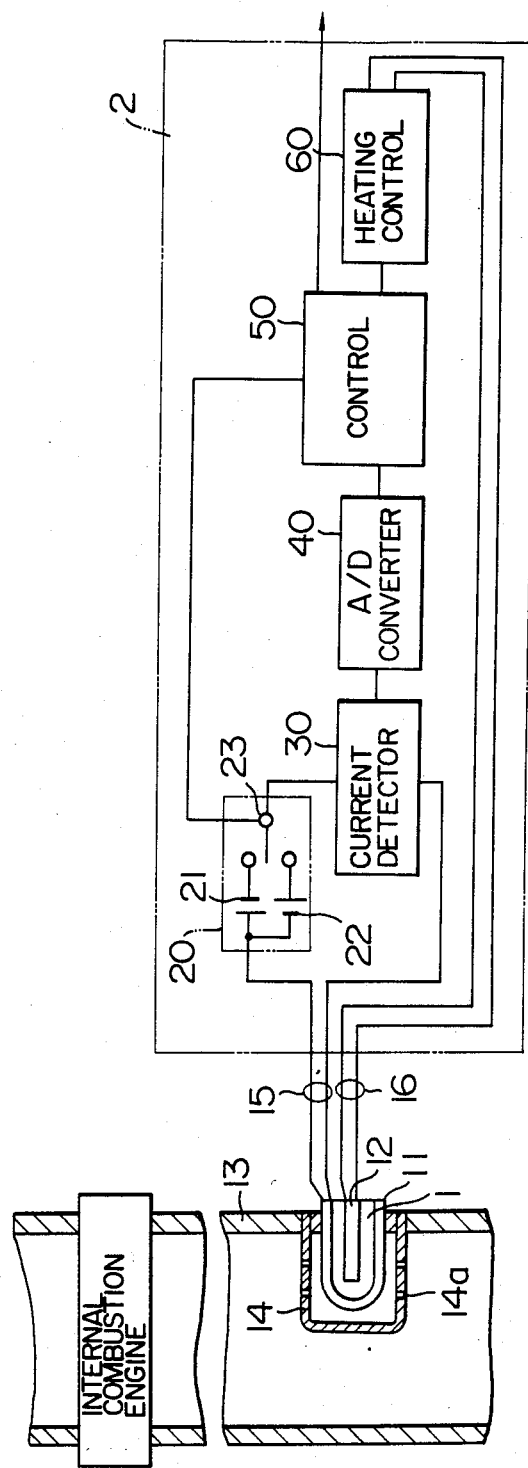
FIG. 1 is a block diagram showing a general configuration of the present invention.

The present invention will be explained below with reference to an embodiment shown in the drawings. FIG. 1 is a diagram showing a general construction of an oxygen concentration detector according to this invention. Reference numeral 1 designates a sensor section, and numeral 2 a control unit. In the embodiment under consideration, the sensor section 1 is mounted within an exhaust pipe 13 of an internal combustion engine, and includes an oxygen sensor of a critical current type 11 with a heater 12 built therein and a cover 14. The cover 14 has small holes 14a for preventing the oxygen sensor 11 from coming in direct contact with the exhaust gas, thereby mechanically protecting and thermally shielding the sensor 11. Numerals 15 and 16 designate lead wires. The heater 12 has a heating capacity (ability) sufficient to activate the oxygen sensor 11.

In the control unit 2, a bias control section 20 includes a positive bias source 21, a negative bias source 22 and switch means 23 for applying a predetermined positive or negative bias to the oxygen sensor in time division. A current detector section 30 is for detecting the output current of the oxygen sensor 11 and an A/D converter section 40 converts the current into a digital value. A control section 50 gives instructions to the bias control section 20 for selecting the positively or negatively biassing condition, and in the process, it checks the output current value produced from the oxygen sensor 11, thereby measuring the critical current (that is, the oxygen concentration) and the sensor temperature (that is, the internal electric resistance of the sensor). A heating control section 60 is provided for controlling the heating condition of the heater 1 in the oxygen sensor 11 in response to the instructions from the control section 50 and in such a manner that the sensor temperature may be included in a predetermined temperature range.

Figure 2:
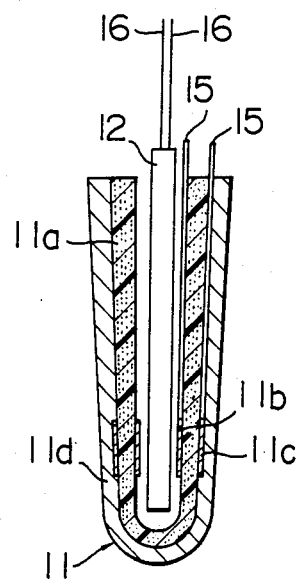
FIG. 2 is a sectional view showing an oxygen sensor of a critical current type.

Now, the construction of the sensor will be specifically explained. In FIG. 2, numeral 11 designates an oxygen sensor, and numeral 11a a solid-electrolyte member in cup shape with an end open and the other end closed. This member 11a has the cup interior of sintered oxide of oxygen ion-conductive material exposed to a reference oxygen such as the atmosphere through an electrode 11b, and has the exterior thereof to a (detection) gas under test through an electrode 11c and a gas-diffusion resistant layer 11d.

Assume, for example, that the sensor 11 includes a single electrode adapted to generate a concentration dependent electromotive force at a stoichiometric air-fuel ratio and a critical current associated with the oxygen concentration on the lean side of the stoichiometric air-fuel ratio. Assume also therefore that the electrode 11c has an area of 10 to 100 mm$^2$ on the gas detection side and a thickness of about 0.5 to 2.0$\mu$. The electrode 11b has on the atmosphere side an area of 10 mm$^2$ or more and a thickness of about 0.5 to 2.0$\mu$, both electrodes being formed of a sufficiently porous precious metal such as platinum with a high catalytic activity by such means as chemical plating, sputtering or paste screen printing. The diffusion resistant layer 11d is formed by such means as plasma flame spray coating of , $Al_2O_3$, $Al_2O_3.MgO$ or $Z_rO_2$, and in order to have a resistance of a predetermined definition against the oxygen diffusion, is formed to 100 to 700$\mu$, 7 to 15% in porosity and 600 to 1200 Å in average pore diameter. The area of the electrode 11c, the thickness, porosity and the average pore diameter of the diffusion resistant layer 11d, on which the critical current value corresponding to the oxygen concentration is dependent, must be controlled and specified at high precision. Numeral 12 designates a heater.

This oxygen sensor 11 is capable of detecting the oxygen concentration linearly. Activation of the sensor, however, requires a high temperature (about 650° C. or higher), and also, due to the narrow range of activation temperature, the activation range cannot be controlled solely by the heating with the exhaust gas of the internal combustion engine.

Figure 3:
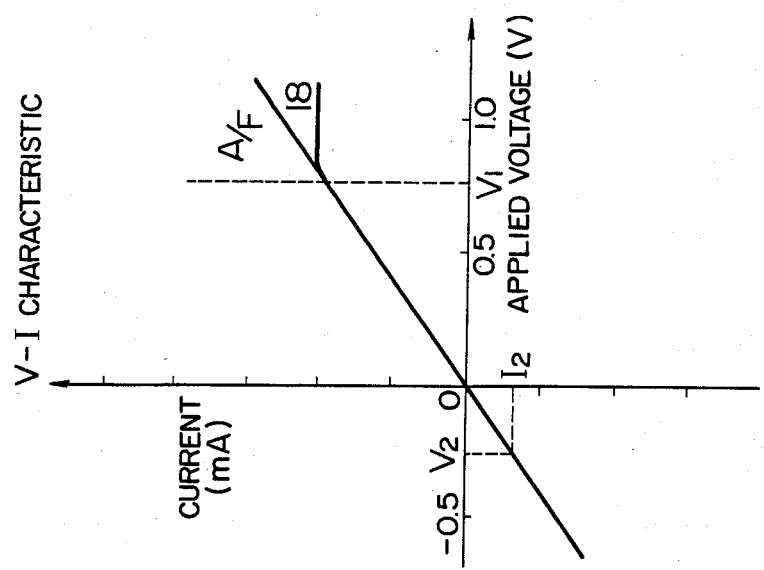
FIGS. 3a and 3b are diagrams showing the V-I characteristic of an oxygen sensor.
Figure 3:
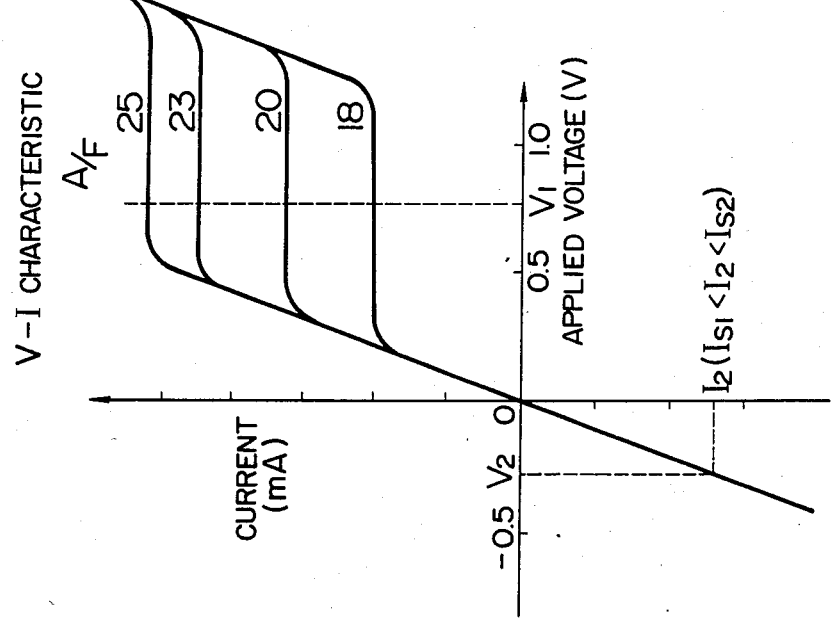

Voltage-current characteristic curves of the oxygen sensor 11 measured by the inventors are shown in FIGS. 3a and 3b. FIG. 3a shows the characteristic curve associated with the active condition of the sensor 11, and FIG. 3b shows the characteristic curve associated with its inactive condition at low temperatures. Upon application of a positive bias voltage $V_1$ of predetermined value under the condition in FIG. 3a (the positive bias voltage being applied by switching the control section 20 to connect the electrode 11c to the positive terminal of the bias source 21 and connect the electrode 11b to the earth line), the current output takes a value proportional to the oxygen partial pressure. In FIG. 3b, on the other hand, such an output proportional to the oxygen partial pressure is not obtainable by the application of the voltage $V_1$. If the sensor 11 is supplied with a negative bias voltage $V_2$, however, the sensor output current does not depend on the oxygen partial pressure but on the temperature. By utilizing this nature, the negative bias voltage $V_2$ is applied to the sensor 11 and the associated sensor current is read, so that the heating amount of the heater 12 is controlled in such a manner that the sensor current takes a predetermined value or a current value within a predetermined range (that is, by making substantially constant the gradient of the linear portion on negative bias side of the characteristic curve). In this way, it is possible to keep the oxygen sensor 11 activated. In other words, referring to FIG. 3a, assuming that the current associated with the applied negative voltage $V_2$ is $I_2$, the heating amount of the heater 12 is increased and so controlled that the current Is changes along a predetermined gradient or falls within a predetermined range from $Is_1$ to $Is_2$. By so doing, the internal resistance of the sensor 11 ($V_2/I_2$) can be made substantially constant.

Even in the case where the oxygen sensor 11 is operated at a predetermined temperature, the inclination of the curve $I_2/V_2$ may change with lapse of time. Such a change may result in that, even under a positive bias voltage $V_1$, the sensor output current can not be measured on a higher or lower side of the oxygen partial pressure. According to the embodiment under consideration, however, the inclination $I_2/V_2$ is detected and controlled to be kept substantially constant, thereby automatically compensating for the change with lapse of time or aging. The control operation of the sensor temperature is effected preferably once every several seconds, for instance, and for the rest of time, the positive bias voltage $V_1$ is applied to measure and output the oxygen partial pressure of the exhaust gas. The time of several seconds is determined by the thermal capacity of the heater 12 and the sensor 11, the maximum amount of heat flowing out of the sensor, and the range of activation temperature.

Now, the operation of the control section 50 in FIG. 1 will be described. In the embodiment under consideration, the control section 50 includes a microcomputer for measuring the oxygen concentration and controlling the sensor temperature in accordance with a predetermined control program.

Figure 4:
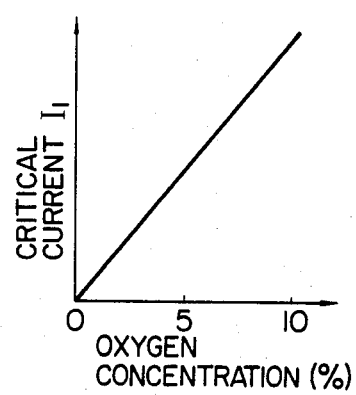
FIG. 4 shows the relation between the critical current of an oxygen sensor and the oxygen concentration.

An example of control flowchart is shown in FIGS. 5a and 5b. A processing (1) in FIG. 5a represents a timer processing or a processing of metering the oxygen concentration started in the main routine, in which step 101 applies a predetermined positive bias (such as 0.7 V) to the oxygen sensor 11, and for this purpose, a positive bias source 21 is connected to the oxygen sensor 11 by operating switch means 23 of the bias control section 20. Step 102 reads the critical current of the oxygen sensor 11 detected by the current detector section 30 through the A/D converter 40. Step 103 determines the oxygen concentration corresponding to the detected critical current value by use of a conversion map between critical current and oxygen concentration (or air-fuel ratio) stored in advance as shown in FIG. 4, and this converted value is stored provisionally in a memory (RAM). In the determination step 103, various methods may be applicable instead of determining the oxygen concentration each time of measurement of the critical current. For example, the average value of the critical current for a predetermined period of time may be determined to be followed by such a determination of the oxygen concentration on the basis of the determined average value, or the error or deviation from the critical current values determined in steps of preceding cycle or the deviation from the average thereof may be determined to correct the oxygen concentration value.

The processing (2) shown in FIG. 5b represents the sensor temperature control started with a timer processing at sufficiently long time intervals. At step 201, in order to apply a predetermined negative bias (such as 0 to −1 V) to the oxygen sensor 11, the negative bias source 22 is connected to the oxygen sensor 11 by operating the switch means 23 of the bias control section 20. Step 202 reads the current $I_2$ flowing through the oxygen sensor 11 from the current detector section 30 by way of the A/D converter section 40. In steps 203 and 204, the sensor temperature is detected from the magnitude of the detected current $I_2$ to determine whether or not the temperature of the oxygen sensor 11 falls within the tolerable active temperature range (such as from 650° C. to 800° C.), and if the sensor temperature is not included in the specified range, the electric power supplied to the heater 11 is controlled through the heating control section 60 to heat the sensor 11.

Figure 7:
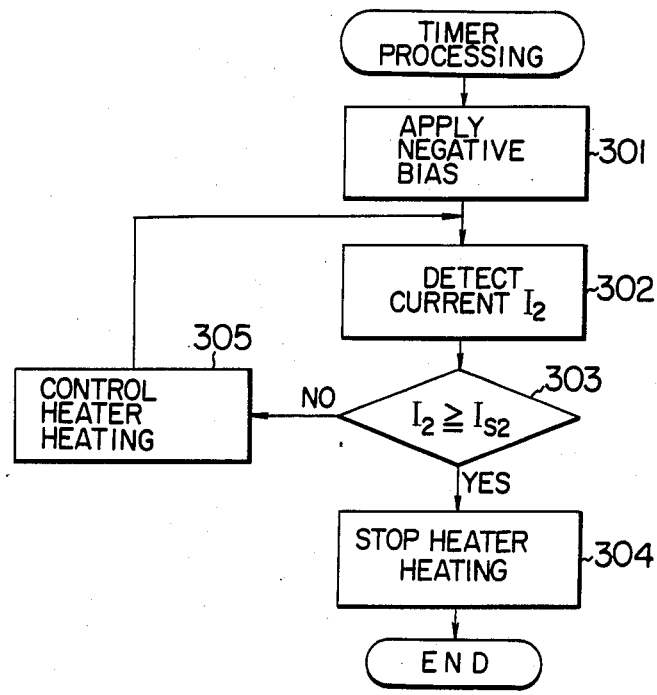

Various methods of heating control of the heater in steps 203 and 204 are available. In some method, the thermal capacity of the sensor 12 or heating capability of the heater 11 may be taken into consideration, and in other methods, the cooling characteristic of the exhaust system or the temperature control intervals are important factors. In an example, as shown in FIGS. 6 and 7, a temperature control interval $T_1$ (interval of timer processings) is set to a length shorter than the cooling time required for the tolerable activation temperature of the oxygen sensor 11 to lower from the upper limit $T_{s2}$ to the lower limit $T_{s1}$. Thus, as shown in FIG. 6(b), the temperature Ts of the sensor 11 can be controlled within the tolerable temperature range $T_{s1}$ to $T_{s2}$ only by controlling the oxygen sensor 11 to the upper limit $T_{s2}$ through heater control at intervals of time $T_1$. FIG. 6(c) shows intervals $T_2$ of measuring the critical current (or oxygen concentration).

FIG. 7 shows a flowchart embodying the above-mentioned method. As shown, the timer processing is started at intervals of time $T_1$. In steps 301 to 303, the negative bias is applied to the oxygen sensor 11 to check whether or not the current $I_2$ has reached a current value $I_{s2}$ corresponding to the upper limit temperature $T_{s2}$ of the sensor. The heating control of the heater is effected until the current value $I_{s2}$ is reached (step 305). When the current value $I_{s2}$ is reached, the process proceeds to step 304 to stop the heating control of the heater.

Figure 8:
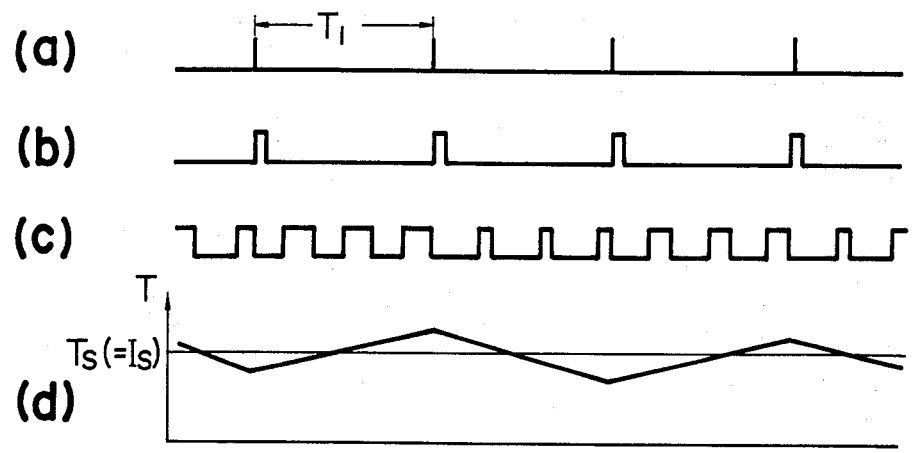
Figure 9:
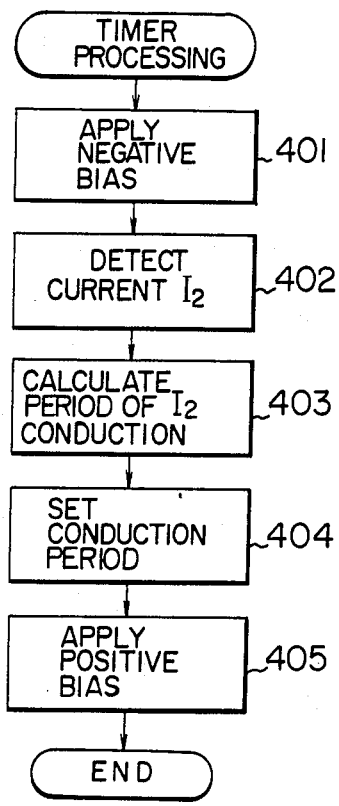
Figure 10:
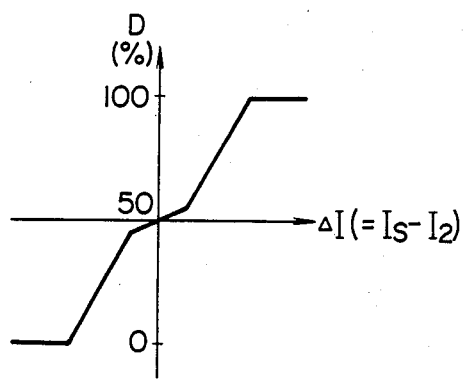

FIGS. 8 to 10 show another method of heating control in which the sensor temperature is regulated to a predetermined value Ts. Specifically, the timer processing is effected at time intervals of $T_1$ so that as shown in steps 401 to 404, the current $I_2$ with the negative bias applied to the oxygen sensor 11 is detected, and the time duration for power application (duty factor) to the heater 12 is calculated from the deviation $\Delta I$ ($=I_s-I_2$) from a predetermined target value $I_s$ at the time points shown in FIG. 8(b). This calculation is made by interpolation of the ($\Delta I - D$) map as shown in FIG. 10 or by processing of calculations. The time duration for the power application thus determined is set at the output section, so that the duty factor of the heater current immediately begins to change in the manner shown in FIG. 8(c). As a result, the sensor temperature changes with respect to the predetermined value Ts in cycles of $T_1$ as shown in FIG. 8(d). The change must be regulated in amplitude at least within ±20° to 30° C. This method permits a stable temperature control since the current $I_2$ is detected only once every period $T_1$ and the heater is controlled all the time with a predetermined duty factor. According to another method of heater control, the temperature Ts of the oxygen sensor 11 is constantly monitored and when the temperature Ts lowers to the lower limit $T_{s1}$, the heater 11 is supplied with current for a predetermined length of time taking the heating capability into consideration thereby to generate heat until the temperature Ts rises in the vicinity of the upper limit $T_{s2}$, or during such a heat generation, the sensor temperature Ts is detected to continue the heat generation until the upper limit $T_{s2}$ is reached. Any of the methods described above may be employed.

Further, in place of the switch means 23 of contact type for the bias control section 20, described above, a proximity switch such as an analog switch may be used with equal effect. Furthermore, instead of using a pair of power supplies including the positive and negative bias sources 21 and 22, a combination of a single power supply and a plurality of operational amplifiers may be used insofar as that the direction of current of the oxygen sensor 11 is made reversible and that the voltage drop across the sensor takes a predetermined value.

Figure 11:
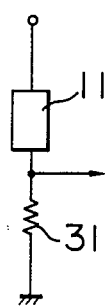
FIGS. 11a and 11b are circuit diagrams showing an example of a current detector 30.
Figure 11:
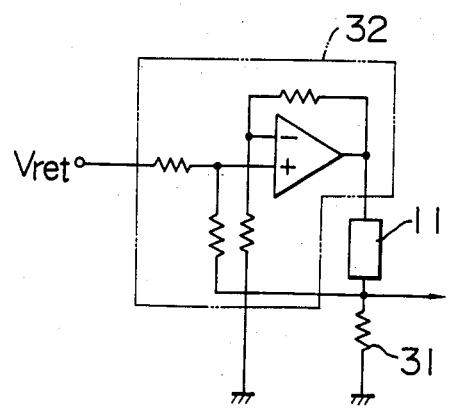

What is more, the current detector section 30 may be constructed in any of various ways. In one configuration, for instance, the current of the oxygen sensor 11 is directly detected by a current detection resistor 31 as shown in FIG. 11a. Alternatively a voltage compensator circuit 32 may be used inserted wherein the voltage drop across the current detection resistor 31 is fed back to an end of the oxygen sensor 11 thereby to maintain the applied voltage of the oxygen sensor 11 constant, as shown in FIG. 11b.

Figure 12:
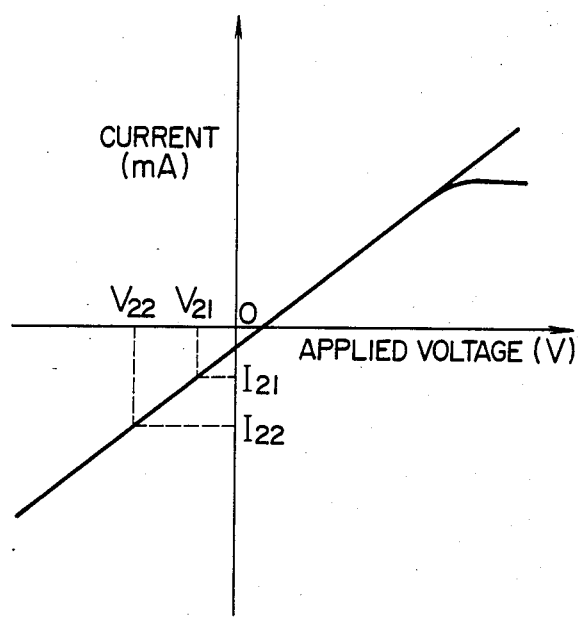
FIGS. 12 and 13 are a V-I characteristic diagram and a flowchart for explaining the present invention.
Figure 13:
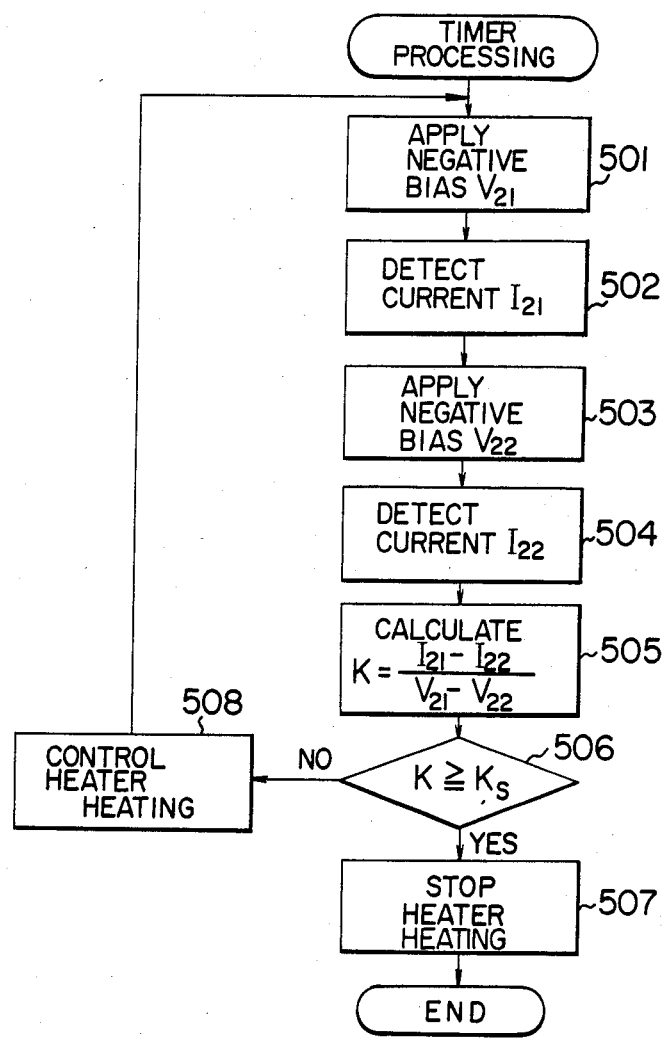

Explanation will be made now of a method of sensor temperature control with reference to FIGS. 12 and 13 against the case where the V-I characteristic curve is displaced by deterioration of the oxygen sensor 11 due to aging. In the case where the zero point of the V-I characteristic curve is displaced as shown in FIG. 12, different negative biases $V_{21}$ and $V_{22}$ are applied to detect sensor currents $I_{21}$, and $I_{22}$, so that the gradient K is determined from $(I_{21}-I_{22})/(V_{21}-V_{22})$ and required to be regulated at a fixed level or within a predetermined range. A typical control flowchart for that purpose is shown in FIG. 13. The gradient K is acquired in steps 501 to 505, followed by steps 506 to 508 in which the heater is controlled until the gradient K reaches a set value Ks thereby to regulate the gradient K to Ks.

The foregoing description concerns the control apparatus for detection of oxygen concentration. In FIG. 1, the control section 50 may be such as to control the ignition timing or the air-fuel ratio by driving an electronically-controlled carburetor or a fuel injection valve by use of one or more parameters including the intake air amount, pressure in intake pipe, throttle valve opening, engine r.p.m., temperature of cooling water or temperature of intake air of the internal combustion engine. In that case, the measured oxygen partial pressure may not be outputted, but may be used for calculation processing in the control section 50 for such controls.

Although the foregoing description is based on the control of the internal combustion engine, the above-mentioned methods may be used with any mechanism for measuring the oxygen partial pressure by use of an oxygen sensor 11.

The heater 12 used for controlling the oxygen sensor 11 to the activation temperature range may be replaced by alternative means such as heating the oxygen sensor 11 by a high-temperature gas and checking the magnitude of the output current of the oxygen sensor 11 as to whether or not the sensor is heated within the activation temperature range.

We claim:

1. An oxygen concentration detector, for detecting the concentration of oxygen in a test gas
   (a) a cup-shaped oxygen sensor made of solid-electrolyte material, the interior of the cup being exposed to a reference gas of a predetermined oxygen concentration through a first electrode, the exterior thereof being exposed to said test gas through a second electrode and a predetermined oxygen-diffusion resistant layer, the sensor being of the limited current type wherein for a predetermined positive bias voltage applied thereto a positve bias current flows therein which current is related to the concentration of oxygen in said test gas;

(b) means for heating said oxygen sensor, (c) current detector means for detecting electric current flowing through said oxygen sensor, (d) bias control means for applying a negative bias of a predetermined DC voltage to said oxygen sensor during a first predetermined period for causing a negative bias temperature measuring current to flow therein and, during a second predetermined period, a positive bias oxygen concentration measuring current to flow therein, and (e) control means for determining internal DC electric resistance of said oxygen sensor in accordance with the negative bias current value detected by said current detector means and controlling the operation of said heating means in accordance with said determined resistance so that said internal electric resistance value reaches a predetermined value.

2. A detector according to claim 1, wherein said heating means is arranged inward of said cup of said oxygen sensor.

3. A detector according to claim 1, wherein said control means includes a microcomputer.

4. A detector according to claim 3, wherein said microcomputer includes means for determining the internal resistance value of said oxygen sensor and adjusting the duty factor of a control signal applied to said heating means at intervals of predetermined time so that said internal resistance value coincides with a predetermined value.

5. An oxygen concentration detector for detecting the concentration of oxygen in a test gas, comprising (a) a cup-shaped oxygen sensor made of solid-electrolyte material, the interior of the cup being exposed to a reference gas of a predetermined oxygen concentration through a first electrode, the exterior thereof being exposed to said test gas through a second electrode and a predetermined oxygen-diffusion resistant layer the sensor being of the limited current type wherein for a predetermined positive bias voltage applied thereto, a positive bias current flows therein which posture bias current is related to the concentration of oxygen in said test gas, (b) heater means for heating said oxygen sensor, (c) bias control means for applying a positive bias of a first voltage to said oxygen sensor during the first period and applying a negative DC bias of a second voltage thereto during a second period, (d) means for detecting electric current flowing through said oxygen sensor, and (e) control means for detecting oxygen concentration in said gas test in accordance with the current value detected by said current detector means for said first period and for detecting the temperature of said oxygen sensor in accordance with the DC current value detected during said second period said control means controlling said heater means so that said detected temperature may be maintained within a predetermined tolerable range.

6. A detector according to claim 5, wherein said control means includes output setting means for detecting deviation between the current value detected during said second period and a set value, and for applying an activating current corresponding to said deviation to said heater means.

7. A detector according to claim 6, wherein said output setting means includes means for generating a pulse signal hhving a duty factor corresponding to said deviation.

8. An oxygen concentration detector for detecting the concentration of oxygen in a test gas, comprising:

(a) a cup-shaped oxygen sensor made of solid-electrolyte material, the interior of the cup being exposed to a reference gas of a predetermined oxygen concentration through a first electrode, the exterior thereof being exposed to said test gas through a second electrode and a predetermined diffusion resistant layer the sensor being of the limited current type wherein for a predetermined positive bias voltage applied thereto, a positive bias current flows therein which positive bias current is related to the concentration of oxygen in said test gas, (b) heater means for heating said oxygen sensor, (c) bias control means for applying a positive bias of a first voltage to said oxygen sensor during a first period, a negative DC bias of a second voltage thereto during a second period, and a negative DC bias of a third voltage thereto during a third period, (d) current detector means for detecting the current flowing through said oxygen sensor, and (e) control means for controlling said oxygen sensor to a predetermined temperature, said control means including first means for detecting the oxygen concentration in said gas under test in accordance with the current value detected by said current detector means during said first period, and second means for detecting deviation between the current values detected by said current detector means during said second and third periods, said second means controlling electric power supplied to said heater means in accordance with said deviation.

9. An oxygen concentration detector for detecting the concentration of oxygen in a test gas, comprising:

(a) an oxygen sensor element including a generally cup-shaped solid-electrolyte material, the interior of the cup being exposed to a reference gas of a predefermined oxygen concentration through a first electrode, the exterior of the cup being exposed to said test gas through a second electrode, and an oxygen-diffusion resistant layer, the sensor exhibiting different voltage-current characteristics depending on whether a positive bias voltage or a negative bias voltage is applied thereto, such that when a predetermined positive bias voltage is applied, a limited current characteristic is exhibited and a positive bias current flows therein which is related to the concentration of oxygen in said test gas, and when a predetermined negative bias voltage is applied, a negative bias current flows which is not related to the oxygen concentration but is related to an internal resistance and hence to a temperature of said oxygen sensor, (b) means for heating said oxygen sensor, (c) current detector means for detecting electric current flowing through said oxygen sensor, (d) bias control means for applying a positive bias or a negative bias of respectively predetermined DC voltage to said oxygen sensor, (e) control means including first means for, at a first time, applying to said oxygen sensor the predetermined positive bias voltage through said bias control means and determining the oxygen concentration in accordance with a limited current value detected by said current detector means, and second means for, at a second time different from said first time, applying to said oxygen sensor the predetermined negative bias voltage through said bias control means and controlling said heating means in accordance with a current detected by said current detector means to achieve a predetermined temperature of said oxygen sensor.

10. An oxygen concentration detector according to claim 9, wherein said second means comprises means for applying a first negative bias voltage and a second negative bias voltage to said oxygen sensor through said bias control means, said receiving data from said current detector means relating to a first current and a second current detected when said first and second negative bias voltages are repsectively applied, and said second control means controls said heating means so that a voltage-current characteristic determined by a first relationship between said first negative bias voltage and said first current and a second relationship between said second negative bias voltage and said second current satisfy a predetermined voltage-current characteristic.

* * * * *

UNITED STATES PATENT AND TRADEMARK OFFICE
CERTIFICATE OF CORRECTION

PATENT NO. : 4,543,176
DATED : September 24, 1985
INVENTOR(S) : HARADA et al

It is certified that error appears in the above-identified patent and that said Letters Patent is hereby corrected as shown below:

Assignee should read:

--Nippondenso Co., Ltd., Kariya, Japan--

Signed and Sealed this

Fifteenth Day of July 1986

[SEAL]

Attest:

DONALD J. QUIGG

Attesting Officer    Commissioner of Patents and Trademarks